(12) United States Patent
Hoeller

(10) Patent No.: US 11,971,379 B2
(45) Date of Patent: Apr. 30, 2024

(54) METHOD FOR PRODUCING A FIBER-PLASTIC COMPOSITE REFERENCE BODY AND TEST METHOD

(71) Applicant: FACC AG, Ried im Innkreis (AT)

(72) Inventor: Helmuth Hoeller, Ried im Innkreis (AT)

(73) Assignee: FACC AG, Ried im Innkreis (AT)

( * ) Notice: Subject to any disclaimer, the term of this patent is extended or adjusted under 35 U.S.C. 154(b) by 557 days.

(21) Appl. No.: 17/267,773

(22) PCT Filed: Sep. 10, 2019

(86) PCT No.: PCT/AT2019/060291
§ 371 (c)(1),
(2) Date: Feb. 10, 2021

(87) PCT Pub. No.: WO2020/051608
PCT Pub. Date: Mar. 19, 2020

(65) Prior Publication Data
US 2021/0190710 A1   Jun. 24, 2021

(30) Foreign Application Priority Data
Sep. 10, 2018   (AT) .............................. A 50764/2018

(51) Int. Cl.
*B29C 33/42*   (2006.01)
*B29C 33/60*   (2006.01)
(Continued)

(52) U.S. Cl.
CPC .......... *G01N 25/72* (2013.01); *B29C 37/0067* (2013.01); *B29C 37/0075* (2013.01);
(Continued)

(58) Field of Classification Search
CPC .......... B29C 33/42; B29C 33/60; B29C 33/68; B29C 37/0067; B29C 37/0075;
(Continued)

(56) References Cited

U.S. PATENT DOCUMENTS 4,494,408 A * 1/1985 DeLacy ......... G01N 2291/0231
264/40.1 X
2007/0028661 A1   2/2007 Girshovich et al.
(Continued)

FOREIGN PATENT DOCUMENTS

CN   102830001 A   12/2012
CN   104407060 A   3/2015
(Continued)

OTHER PUBLICATIONS

ISA European Patent Office, International Search Report Issued in Application No. PCT/AT2019/060291, dated Jan. 14, 2020, WIPO, 2 pages.
(Continued)

*Primary Examiner* — Leo B Tentoni
(74) *Attorney, Agent, or Firm* — McCoy Russell LLP

(57) ABSTRACT

The invention relates to a method for producing a fiber-plastic composite reference body for simulating delamination for the nondestructive testing of FPC components, in particular aircraft components, comprising the following steps: i. producing a first insert by a. arranging a first FPC layer; b. forming a recess in the first FPC layer; c. procuring the first FPC layer, in order to obtain the first insert; ii. producing a second insert by a. arranging a second FPC layer; b. pre-curing the second FPC layer, in order to obtain the second insert; iii. providing at least one first FPC layer and at least one second FPC layer with a first clearance and a second clearance; iv. inserting the first insert and the second insert into the respective clearance of the corre-
(Continued)

sponding FPC layer; v. curing the arrangement, a delamination being simulated at the recess of the first insert.

19 Claims, 5 Drawing Sheets

(51) Int. Cl.
    *B29C 33/68*     (2006.01)
    *B29C 37/00*     (2006.01)
    *B29C 70/30*     (2006.01)
    *B29C 70/54*     (2006.01)
    *B29C 70/68*     (2006.01)
    *B32B 3/30*     (2006.01)
    *B32B 5/26*     (2006.01)
    *B64F 5/60*     (2017.01)
    *G01N 25/72*     (2006.01)
    *G01N 29/04*     (2006.01)
    *G01N 29/30*     (2006.01)
    *B29L 31/30*     (2006.01)
    *B29L 31/40*     (2006.01)
    *G01N 33/00*     (2006.01)

(52) U.S. Cl.
CPC ............ B29C 70/545 (2013.01); B29C 70/68 (2013.01); B29C 70/682 (2013.01); B29C 70/683 (2013.01); B29C 70/685 (2013.01); B32B 3/30 (2013.01); B32B 5/26 (2013.01); B64F 5/60 (2017.01); G01N 29/043 (2013.01); *B29C 2037/90* (2013.01); *B29C 2793/0018* (2013.01); *B29C 2793/0081* (2013.01); *B29L 2031/3076* (2013.01); *B29L 2031/40* (2013.01); *B32B 2307/732* (2013.01); *B32B 2605/18* (2013.01); *G01N 2033/0003* (2013.01); *G01N 2203/0091* (2013.01); *G01N 2291/0231* (2013.01); *G01N 2291/0289* (2013.01)

(58) Field of Classification Search
CPC ... B29C 2037/90; B29C 70/30; B29C 70/545; B29C 70/68; B29C 70/682; B29C 70/683; B29C 2793/0018; B29C 2793/0081; B29L 2031/40; B64F 5/60; G01N 25/72; G01N 29/043; G01N 29/30; G01N 2033/0003; G01N 2203/0091; G01N 2203/0298; G01N 2291/0231; G01N 2291/0289
USPC .............. 264/40.1, 154, 258, 338, 407, 410; 73/150 A, 587, 588; 374/4
See application file for complete search history.

(56) References Cited

U.S. PATENT DOCUMENTS

| 2012/0069865 | A1 | | 3/2012 | Ladru et al. |
| 2014/0272324 | A1 | | 9/2014 | Chen et al. |
| 2014/0346405 | A1 | | 11/2014 | Ferguson et al. |
| 2018/0292307 | A1 | * | 10/2018 | Juarez ................... G01N 29/30 |

FOREIGN PATENT DOCUMENTS

| CN | 106796205 | A | | 5/2017 | |
| CN | 108008013 | A | | 5/2018 | |
| EP | 1750123 | A2 | | 2/2007 | |
| EP | 2431736 | A1 | | 3/2012 | |
| EP | 2572871 | A2 | | 3/2013 | |
| EP | 2769834 | A1 | * | 8/2014 | ...... G01N 2203/0298 |
| EP | 3193164 | A1 | | 7/2017 | |
| FR | 3068473 | B1 | * | 7/2019 | ............ G01N 29/30 |
| JP | S61265565 | A | | 11/1986 | |
| JP | 5565210 | B2 | | 8/2014 | |
| WO | 2016066512 | A1 | | 5/2016 | |

OTHER PUBLICATIONS

State Intellectual Property Office of the People's Republic of China, Office Action and Search Report Issued in Application No. 201980058979.9, dated Jul. 31, 2023, 11 pages. (Submitted with Partial Translation).

Intellectual Property India, Examination Report Issued in Application No. 202117009301, dated Jun. 7, 2021, 5 pages.

* cited by examiner

METHOD FOR PRODUCING A FIBER-PLASTIC COMPOSITE REFERENCE BODY AND TEST METHOD

CROSS REFERENCE TO RELATED APPLICATIONS

The present application is a U.S. National Phase of International Application No. PCT/AT2019/060291 entitled "METHOD FOR PRODUCING A FIBRE-PLASTIC-COMPOSITE REFERENCE BODY AND TEST METHOD," and filed on Sep. 10, 2019. International Application No. PCT/AT2019/060291 claims priority to Austrian Patent Application No. A 50764/2018 filed on Sep. 10, 2018. The entire contents of each of the above-listed applications are hereby incorporated by reference for all purposes.

TECHNICAL FIELD

The invention relates to a method for producing a fiber-plastic composite (FPC) reference body for simulating a delamination for the nondestructive testing of FPC components, in particular aircraft components.

BACKGROUND AND SUMMARY

The invention further relates to a method for the nondestructive testing of an FPC component, in particular an aircraft component.

In the production of safety-critical fiber-plastic composite (FPC) components, for example such as aircraft components, the subsequent verification and registration of component defects is of special importance. For this purpose, use is usually made of nondestructive test methods (English: "non-destructive testing", NDT for short), in order to be able to detect defective components right away on the one hand, and to not have the test method itself damage non-defective components on the other hand. In order to be able to also draw conclusions about potential defect sources in production during the test method, detected component defects are allocated to a defect type or defect class. For comparison and calibration purposes, reference bodies with specifically incorporated artificial component defects are produced to this end, and measured with the help of an NDT method. In order to ensure the precise allocation of a component defect to a defect class in the process, the artificial component defects in the reference bodies, which component defects serve as a reference, must simulate the production defects of the test specimens as precisely as possible.

However, most component defects are difficult if not impossible to simulate without the help of foreign bodies, and artificial component defects, depending on defect type, have thus far deviated to more or less an extent from the defects of the test specimens in terms of composition. In particular a so-called delamination, i.e., a local, flat separation of two FPC layers in a partial area of an FPC component with air inclusion, can to date not be satisfactorily simulated without introducing foreign bodies. Component defects other than delamination also exist, and include in particular layer porosity and volume porosity. In layer porosity, a concentrated accumulation of microscopic and macroscopic gas or air inclusions takes place in the matrix or connecting means of the FPC material between the two FPC layers of a component. A 2D-component defect is thus present. In volume porosity, an accumulation of gas or air inclusions in the matrix or connecting means of the FPC material takes place in several FPC layers of a component, in particular essentially over the entire cross section of the FPC laminate. A 3D-component defect is thus involved. Since a delamination, i.e. a flat separation of FPC layers, can have serious consequences in aircraft components, it is extremely important that a delamination be detected, and thus that reference bodies that simulate the delamination as realistically as possible be generated.

Various methods for simulating component defects are known from prior art. For example, EP 3 193 164 A1 describes a method in which component defects can be introduced into FPC parts with the help of an expansion body. To this end, the expansion body is placed between several layers of FPC material, resin is added, and then heated. Due to the high expansion coefficient of the expansion body, it shrinks to a greater extent than the FPC material surrounding it while cooling, and thereby generates a large permanent cavity. The expansion body subsequently remains in the component as a foreign body.

In CN104407060 a porosity of the material is simulated with the help of glass beads, which are introduced into the material during the production process. However, these likewise remain in the material.

Furthermore, other methods for simulating component defects are known from EP 1 750 123 A2, EP 2 431 736 A1 and US 2014/0272324 A1.

In addition, a method for generating porosity in composites is known from US 2014/0346405 A1. To this end, the composite materials are subjected to different curing methods, so as to in this way generate varying porosity levels by escaping gases.

The disadvantage to prior art is that a delamination, meaning a flat separation of individual FPC layers within an FPC component, cannot be simulated satisfactorily or without foreign bodies. Among other things, the foreign bodies here distort the measurement result.

As a consequence, the object of the invention is to ameliorate or eliminate at least several disadvantages of the prior art. Therefore, the goal of the invention in particular is to create a method which enables the realistic simulation of a delamination at defined locations in an FPC reference body.

The set object is here achieved by a method with at least the following steps:
i. Producing a first insert for the FPC reference body by
  a. arranging a first FPC layer;
  b. forming a recess in the first FPC layer;
  c. precuring the first FPC layer to obtain the first insert for the FPC reference body;
ii. Producing a second insert for the FPC reference body by
  a. arranging a second FPC layer;
  b. precuring the second FPC layer to obtain the second insert for the FPC reference body;
iii. Providing at least one first FPC film with a first clearance and at least one second FPC film with a second clearance;
iv. Inserting the first insert into the first clearance of the first FPC film and inserting the second insert into the second clearance of the second FPC film;
v. Curing the arrangement comprised of the first FPC film with the first insert and the second FPC film with the second insert, wherein a delamination is simulated at the recess in the first FPC layer of the first insert.

The method according to the invention advantageously enables the specific introduction of a(n artificial) delamination into an FPC reference body consisting of FPC material. Since the method according to the invention can be used to generate the delamination without introducing a foreign body, i.e., a substance that does not consist of FPC material and is not present on the component to be compared, the FPC reference body is especially suitable for realistically simulating a delamination for the FPC components to be tested, in particular for the aviation industry. Among other things, the simulated delamination can be used for calibration purposes by subjecting the FPC reference body to an NDT measurement process, for example a thermography process. Due to the realistic composition of the simulated delamination, the measurement results obtained from the reference body are especially suitable as comparison or reference values for the NDT testing of FPC components. Since foreign bodies, i.e., parts that do not consist of FPC material and are not present on the component to be compared, need not be used when generating the FPC reference body, measurement curves can be recorded for the FPC reference body that correspond very precisely with those of components having a "natural" delamination, i.e., one that arose during serial production. As mentioned at the outset, a delamination is a local, flat separation of two FPC layers in a partial area of an FPC component with air inclusion. By contrast, only a partial separation of the FPC layers takes place in case of a layer porosity. In the case of volume porosity, the separation takes place over several FPC layers with air inclusion.

For purposes of the disclosure, an FPC film also constitutes an FPC layer. As in the FPC components to be tested, the individual FPC layers in the FPC reference body are preferably formed of fibers that are loose or bonded into fabric and impregnated with resin or another connecting means.

The connecting means can serve to connect the fibers within an FPC layer, to connect the FPC layers with each other, and to connect the FPC films with the precured inserts. Among other things, the FPC material provided for all FPC layers can be CFP (carbon fiber-reinforced plastic), FGP (fiberglass-reinforced plastic) or aramid fiber composite, in particular CFP, FGP or aramid fiber composite processed into a prepreg.

In the method according to the invention, the delamination is generated by inserting the (precured) inserts into the respective corresponding clearance of the FPC films and curing the adjacent arrangement comprised of a first and second FPC film, preferably under pressure. The first and the second clearances are advantageously cut into the first or second FPC film with a knife or another cutting tool, and preferably have essentially the shape or contour of the outer edge of the first or the second insert. The connecting means for connecting the inserts, for example resin or some other connecting means, is preferably already contained in the FPC films. By connecting the first and second FPC film and pressing the two FPC films against each other along with the inserts, in particular during the curing process, the connecting means is sucked by the capillary effect into a narrow joining gap lying between the first and second insert up until the recess, and thereby connects the two inserts in an edge area outside of the recess, both with each other and with the FPC films. Therefore, the connecting means gets from the FPC film between the precured inserts so as to connect the inserts.

At the boundary of the recess or of the enclosed cavity, the suction effect of the capillary effect finally comes to a standstill owing to the greater distance between the two inserts, and the connecting means is essentially not pulled into the recess. As a consequence, the recess is essentially free of connecting means, and the first and second FPC films do not adhere to each other in the area of the recess, so that the simulated delamination can arise via curing. In the areas outside of the recess, the sucked-in connecting means yields a positive and nonpositive connection between the inserts or the first and second FPC films. In terms of material composition, an FPC film essentially corresponds to an FPC layer.

After the inserts have been inserted into the respective clearances and the FPC films have been connected, the opening of the recess of the first insert faces the second insert. In addition, it is favorable that the FPC films be connected in such a way that the clearances of the FPC films abut against each other in essentially a congruent manner. For this purpose, the clearances and the inserts are preferably essentially the same size. In addition, it is important that the first insert be inserted into the first clearance in such a way as to form a cavity bounded by the recess of the first insert and by the second insert, the so-called air pocket.

In the method according to the invention, the first and the second inserts are inserted into the respective clearances in a precured state. In this conjunction, precured means that the two parts are cured to such an extent that they essentially retain their shape automatically for the other procedural steps. The first curing steps of a curing process suitable for the used FPC material can be used for precuring, i.e., the curing process can be ended as soon as the parts have been cured to such an extent that they essentially retain their shape automatically for the other procedural steps. After the first FPC film has been connected with the second FPC film and the inserts have been inserted into the corresponding clearances, the arrangement comprised of the first and second FPC films is completely cured, which results in the simulated delamination. In this conjunction, curing means that the first and second FPC films are completely cured, including the inserts and connecting means. The first and second clearances preferably comprise essentially the shape or contour of the outer edge of the first or second insert. Therefore, the inserts also comprise essentially the same dimensions as the respective clearances.

In order to generate an especially realistic FPC reference body of any thickness, at least one FPC base layer can be provided on the one side of the arrangement comprised of the first and second FPC film and/or at least one final FPC layer can be provided on the other side of the arrangement comprised of the first and second FPC film. Adding any number of FPC base layers and/or the final FPC layers makes it possible to generate an FPC reference body of any thickness. The number of final FPC layers and FPC base layers can here differ from each other. The method according to the invention thus makes it possible to arrange the cavity or artificial delamination at any depth desired within the FPC reference body at a location provided for this purpose. Depending on the application, several delaminations (air pockets) can be provided. The other air pockets can be designed in the same way as described above, i.e., by means of first and second inserts.

In order to facilitate the capillary effect and generate an especially realistic delamination, it is advantageous that the first insert comprises a circumferential and preferably essentially even peripheral surface around the recess. In this conjunction, circumferential means that the recess is surrounded on all sides by the peripheral surface. In this way, connecting means can be sucked uniformly into the joining gap lying between the two inserts from all sides. The peripheral surface can suitably be designed symmetrically around the recess. In order to adjust the peripheral surface to a specific shape or remove unnecessary partial areas of the peripheral surface, it can be provided that the peripheral surface be at least partially trimmed with a corresponding cutting tool.

In the course of the invention, it was found that especially favorable dimensions exist for the inserts, with which dimensions the capillary effect can be regulated to such an extent that enough connecting means for sufficiently connecting the inserts is sucked into the joining gap on the one hand, and that entry by the connecting means into the cavity can be prevented on the other. For this purpose, it is favorable that the peripheral surface be designed symmetrically around the recess, and that the ratio between the constant width of the circumferential peripheral surface and the width of the opening cross sectional surface of the recess bordered by the circumferential peripheral surface measures essentially between 0.1 and 10, in particular essentially between 2 and 8. Therefore, the width of the circumferential peripheral surface is preferably wider than the opening cross sectional surface. These dimensions result from the knowledge that too little connecting means is sucked into the gap between the inserts given too wide a peripheral surface, while connecting means disadvantageously gets into the cavity given too narrow of a peripheral surface. In addition, tests have demonstrated that the deeper the recess comes to lie in the arrangement comprised of the first and second FPC films, i.e., the more FPC base layers/final layers are arranged above or below the recess, the higher the ratio selected must be. The width of the opening cross sectional surface relates to the maximum distance between two edge points of the opening cross sectional surface. Given a circular opening cross sectional surface, the width corresponds to the diameter of the opening cross sectional surface. The width of the circumferential peripheral surface relates to the maximum distance between the inner edge of the peripheral surface, the inner edge bordering the opening cross sectional surface, and the outer edge of the peripheral surface, the outer edge coinciding with the outer edge of the insert. In this embodiment, the recess is essentially located centrally on the first insert, so that the peripheral surface is designed symmetrically around the recess.

A preferred embodiment provides that the maximum height of the recess be smaller than the thickness of the first FPC film, in particular smaller than the thicknesses (i.e., vertical (height) extensions) of all FPC films and FPC layers. This makes it possible to reduce a bulging of FPC films or FPC layers lying thereover. In an especially preferred embodiment, all FPC layers and FPC films used in the FPC reference body comprise essentially the same layer thickness. This embodiment preferably provides that the height of the recess be smaller than the used layer thickness.

A preferred embodiment variant provides that the recess be formed by applying the first FPC layer on a molding tool before precuring the first FPC layer. To this end, the first FPC layer is placed on the molding tool in an uncured, i.e., moldable state. Precuring then causes the recess to remain in the first FPC layer, and hence in the first insert.

In order to form the recess in an especially easy way, a plate part, in particular a small metal plate, is provided as the molding tool in a first embodiment. This small metal plate is again removed after precuring the FPC layer, and can advantageously be reused.

In an alternative embodiment variant, a projection on a mold carrier is provided as the molding tool. To this end, the first FPC layer is placed on the mold carrier and projection in an uncured state, thereby forming the recess. After precuring, the FPC layer is taken off of the mold carrier.

In order to facilitate the detachment of precured FPC layers, it is advantageous that, prior to insertion into the clearance, the molding tool be provided with a release agent, in particular a liquid release agent or a separating foil. As a result, the molding tool can be removed without damaging the first or second FPC layer. Naturally, such a release agent can also be provided to other parts, for example mold carriers, so that all FPC components can be easily detached.

A preferred embodiment provides that another recess be formed in the second FPC layer. In this way, the cavity, and hence the air inclusion, of the delamination can advantageously be enlarged. If the second insert has another recess, the second insert is preferably inserted into the second clearance in such a way that the opening of the other recess of the second insert faces the first insert. The FPC films or inserts are advantageously aligned in such a way that the openings of the recesses lie essentially opposite each other, and together include an air volume in a cavity formed by the recesses. In an especially preferred form, the first and second inserts are essentially identical in design. All statements and production steps in this disclosure that relate to the recess of the first insert can be applied to the other recess in the second insert.

The FPC reference body described above can be used for the NDT testing of FPC components.

The method for the nondestructive testing of an FPC component, in particular an aircraft component, comprises at least the following steps:

Producing a fiber-plastic composite (FPC) reference body as described before;

Testing the FPC component with a nondestructive test method, for example a thermographic method; and Comparing measurement results from the nondestructive test method for the FPC component with reference values for the FPC reference body.

BRIEF DESCRIPTION OF THE FIGURES

The invention will be described in more detail below based on preferred embodiments.

DETAILED DESCRIPTION

The figures show individual procedural steps for manufacturing an FPC reference body 26, which can be used during the NDT testing of FPC components, such as aircraft wings or aircraft flaps.

Figure 1:
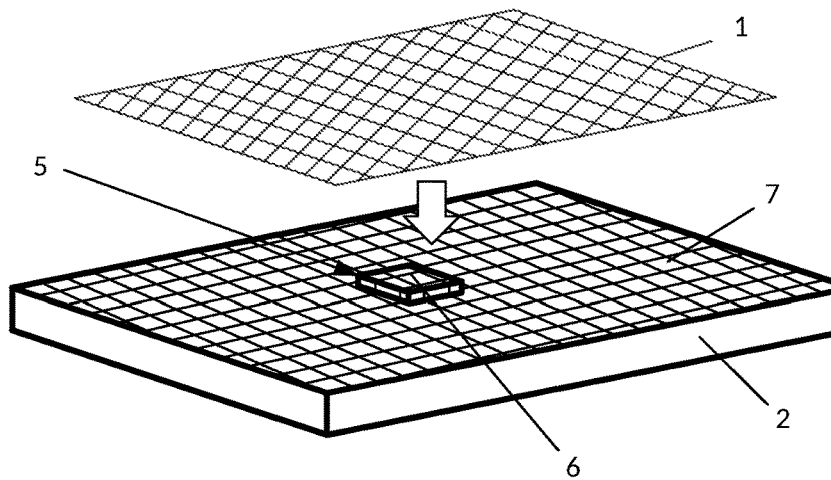
FIG. 1 shows the placement of a first FPC layer on a mold carrier for producing the first insert.
Figure 2:
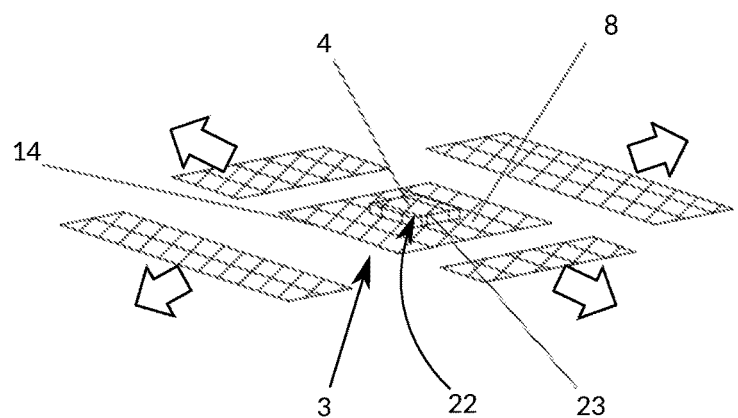
FIG. 2 shows a first and second insert.

FIG. 1 shows an uncured first FPC layer 1, which is placed on a mold carrier 2 in the direction of the arrow, so as to produce a first insert 3 with a recess 4 (see FIG. 2). As usually the case especially for aircraft components, the first FPC layer 1 consists preferably of CFP, FGP or aramid fibers, in particular of CFP, FGP or aramid materials processed into prepregs. In order to generate the recess 4, a molding tool 5 in the form of a projection 6 on the mold carrier is preferably provided on the mold carrier 2. By applying the uncured first FPC layer 1 onto the mold carrier 2, it essentially adapts to the shape of the mold carrier 2, in particular to the projection 6, and forms the recess 4. For example, a small metal plate can also be provided as the molding tool 5 in place of the projection 6. The mold carrier 2 prescribes the subsequent shape of the pre cured FPC layers, preferably an essentially flat surface 7 as in FIG. 1.

After the first FPC layer 1 was placed on the mold carrier 2 and the recess 4 was formed, the first FCP layer 1 is precured using corresponding procedures known to the expert, while the molding tool 5 remains in the formed recess 4. For example, such a precuring procedure can be implemented via the first steps of a curing procedure in an autoclave (not shown). As the result of precuring, the first insert 3 essentially automatically retains its shape for the other procedural steps.

FIG. 2 shows a precured first insert 3 with the recess 4 and a circumferential (continuous) peripheral surface 8 formed symmetrically around the recess 4. The recess 4 is arranged essentially centrally in the first insert 3, and (on the lower side of the first insert 3 better visible on FIG. 4a and FIG. 4b) comprises an opening 22 and an opening cross sectional surface 23 that corresponds to the surface of the opening 22 in the plane of the peripheral surface 8. The opening cross sectional surface 23 is bounded by the peripheral surface 8. The arrows denote that the circumferential peripheral surface 8 is partially trimmed and removed, for example by a suitable cutting tool (not shown), so as to adjust the insert 3. Depending on starting material, it is not absolutely necessary to trim the peripheral surface 8.

Figure 4A:
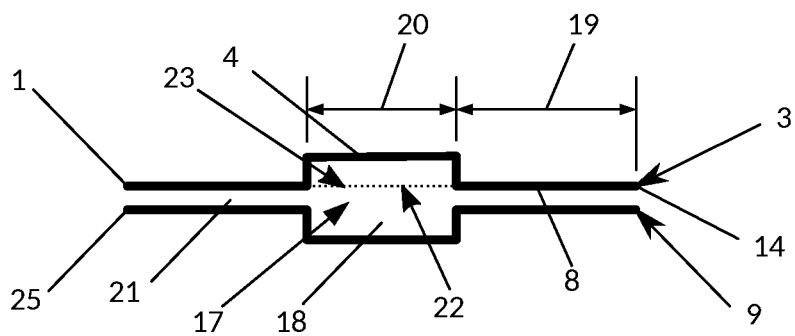
FIG. 4a-4b each show two inserts in cross section.
Figure 4B:
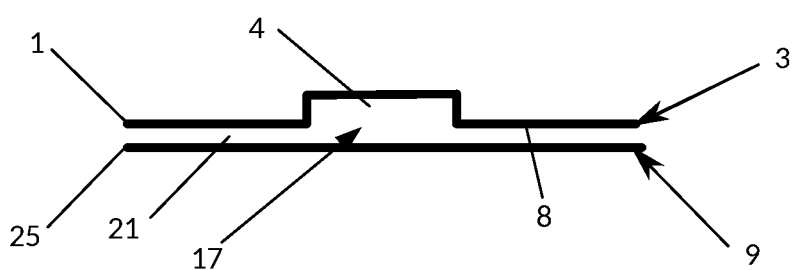

The same procedural steps as for the first insert 3 can be performed in order to generate a second insert 9 out of a second FPC layer 25 (see FIG. 4a and FIG. 4b). In this way, a second insert 9 can be generated that is essentially identical to the first insert 3. However, it can also be provided that the second insert 9 have no recess, i.e., that it be essentially flat in design. To this end, the second FPC layer 25 can be placed on a mold carrier 2 without a molding tool 5 and precured. The second insert 9 fabricated in this way has an essentially planar surface, and is free of bulges.

Figure 3A:
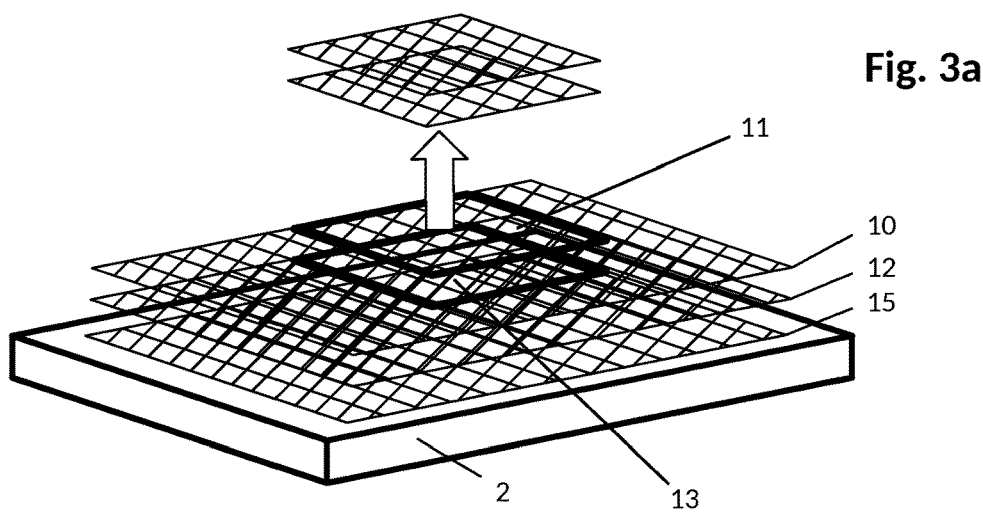
FIG. 3a-3b shows the insertion of the inserts into the respective FPC films.

FIG. 3a shows a first FPC film 10 with a first clearance 11 and a second FPC film 12 with a second clearance 13. The clearances 11, 13 are here best cut into the first or second FPC film 10, 12 with a knife or some other cutting tool (not shown). The arrow once again denotes the removal of excess sections. The clearances 11, 13 preferably have the shape or the contour of the outer edge 14 of the first 3 or second insert 9 for the subsequent insertion of the inserts. In addition, it is provided that the first FPC film 10 be connected with the second FPC film 12 in such a way that the clearance 11, 13, and thus later on the inserts 3, 9, essentially lie congruently on top of each other. The clearances 11, 13 and the inserts 3, 9 are preferably the same size, so that the inserts 3, 9 can be inserted flush into the respective clearances 11, 13.

Figure 3B:
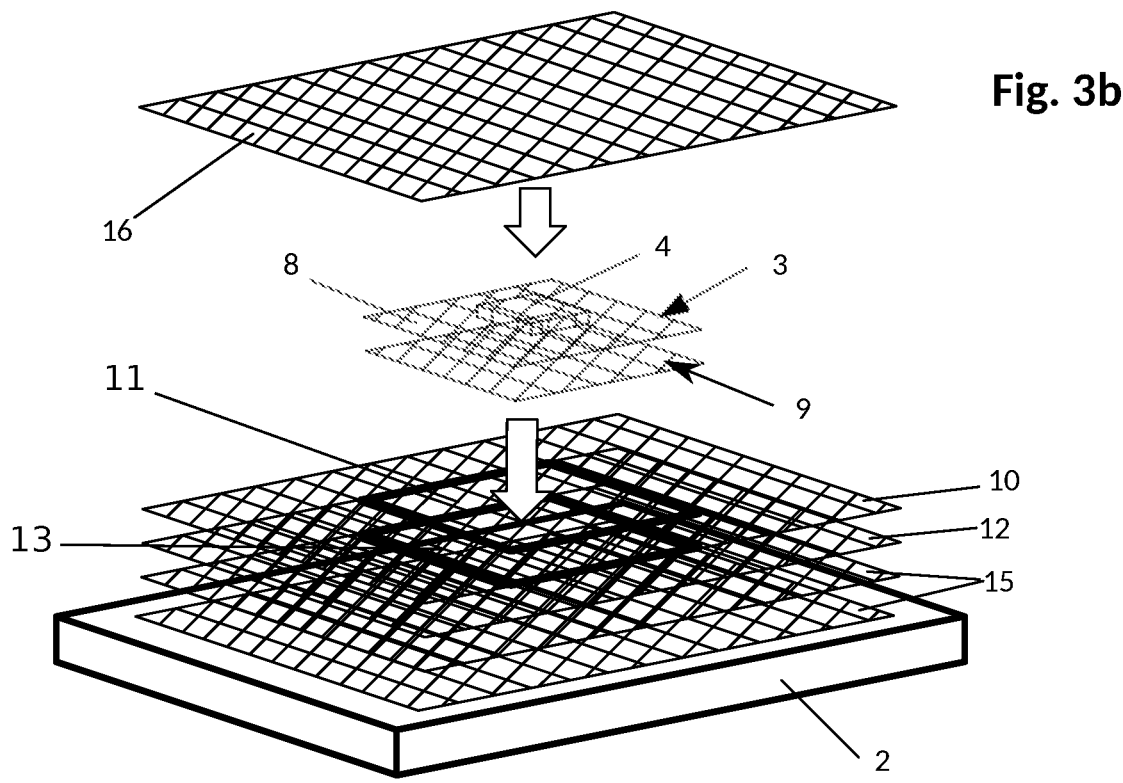

In order to improve the fixation of the inserts 3, 9 and generate an especially realistic FPC reference body 26 in which the delamination is arranged at any depth within the FPC reference body 26, at least one FPC base layer 15 (FIG. 3a depicts one FPC base layer 15 and FIG. 3b depicts two FPC base layers 15) is provided on the one side of the arrangement comprised of a first 10 and second 12 FPC film. On FIG. 3b, at least one final FPC layer 16 is further provided on the other side of the arrangement comprised of a first 10 and second 12 FPC film. The entire arrangement is likewise placed on a mold carrier 2 for subsequent curing. The arrows once again denote the assembly of the subsequent FPC reference body.

FIG. 3b shows the insertion of the first insert 10 into the first clearance 11 of the first FPC film 10 and the insertion of the second insert 9 into the second clearance 13 of the second FPC film 12. It is here important that the first 3 and the second 9 insert be inserted into the respective clearances 11, 13 in such a way as to form a cavity 17, the so-called air pocket, bordered by the recess 4 of the first insert 3 and the second insert 3, as visible on FIGS. 4a and 4b. The opening 22 of the recess 4 of the first insert 3 here faces the second insert 9. If the second insert 9 comprises a further recess 18, the second insert 9 is likewise inserted into the second clearance 13 in such a way that the opening of the other recess 18 of the second insert 9 faces the first insert 3. It is also essential that the first 3 and second 9 insert or the clearances 11, 13 lie essentially congruently next to each other.

FIG. 4a shows the first insert 3 and an essentially identical second insert 9 with a further recess 18. The two inserts 3, 9 are arranged in such a way as to form a cavity 17 bordered by the recesses of the first and second inserts 3, 9. The opening 22 of the recess 4 of the first insert 10 here faces the second insert 9, while the opening of the additional recess 18 of the second insert 12 faces the first insert 10. As illustrated on FIG. 4a, the circumferential peripheral surface 8 of the inserts 3, 9 comprises a width 19 between the inner edge bordering the opening cross sectional surface 23 of the recess 4 and the outer edge 14 of the peripheral surface 8 or of the insert. The opening cross sectional surface 23 of the recess 4 is denoted by the dashed line 23. The opening cross sectional surface 23 of the recess 4 bordered by the circumferential peripheral surface 8 further has a width 20 that relates to the maximum width in the case of noncircular opening cross sectional surfaces 23. The ratio between the width 19 of the peripheral surface 8 and the width 20 of the opening cross sectional surface 23 preferably measures essentially between 0.1 and 10, in particular essentially between 2 and 8.

FIG. 4b shows an embodiment in which the second insert 9 has no other recess. The second insert 9 is essentially flat in design, i.e., free of bulges.

Figure 5A:
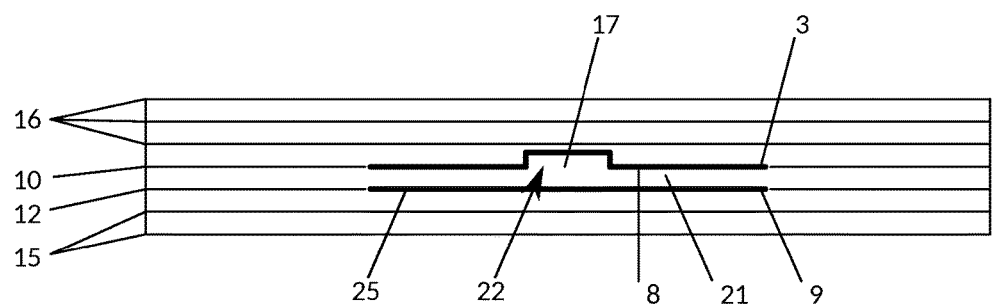
FIG. 5a-5c show the formation of a delamination.
Figure 5B:
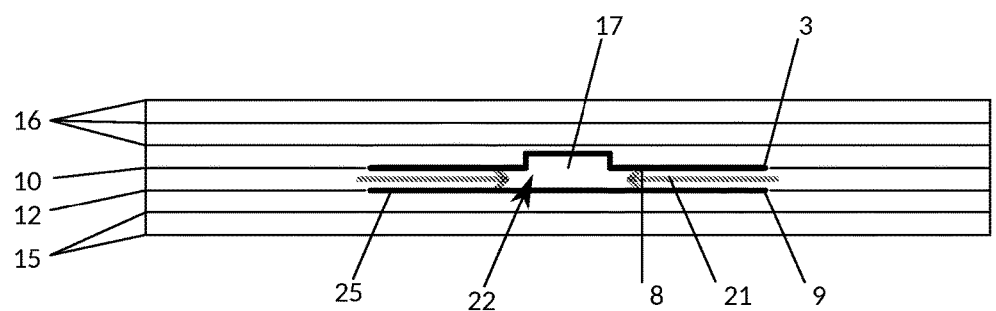
Figure 5C:
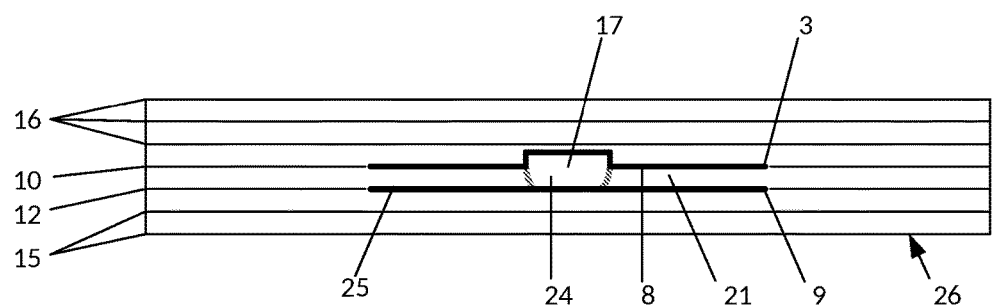

FIG. 5a shows the arrangement comprised of the first FPC film 10 with the first insert 3 and the second FPC film 12 with the second insert 9. By applying contact pressure, in particular during a curing process suitable for the FPC material, connecting means contained in the used FPC material is sucked by the capillary effect in the direction of the arrow into a narrow joining gap 21 lying between the first and second insert 3, 9 up to the recess, and in so doing connects the two inserts 3, 9 with each other in the peripheral surface 8 outside of the recess 4, as well as with the first 10 and second 12 FPC films 12. The connecting means is thus made available for connecting the inserts 3, 9 by the FPC films. As depicted on FIG. 5c, the suction effect of the capillary effect finally essentially comes to a standstill at the boundary to the recess 4 or the included cavity 17 owing to the greater distance between the two inserts 3, 9, and the connecting means is not pulled into the recess 4 or cavity 17. As a consequence, the recess 4 is essentially free of connecting means, and the first and second inserts 3, 9 do not adhere to each other in the area of the recess 4. As a result, the simulated delamination 24 is formed in the recess 4 or in cavity 17 after curing.

Figure 6:
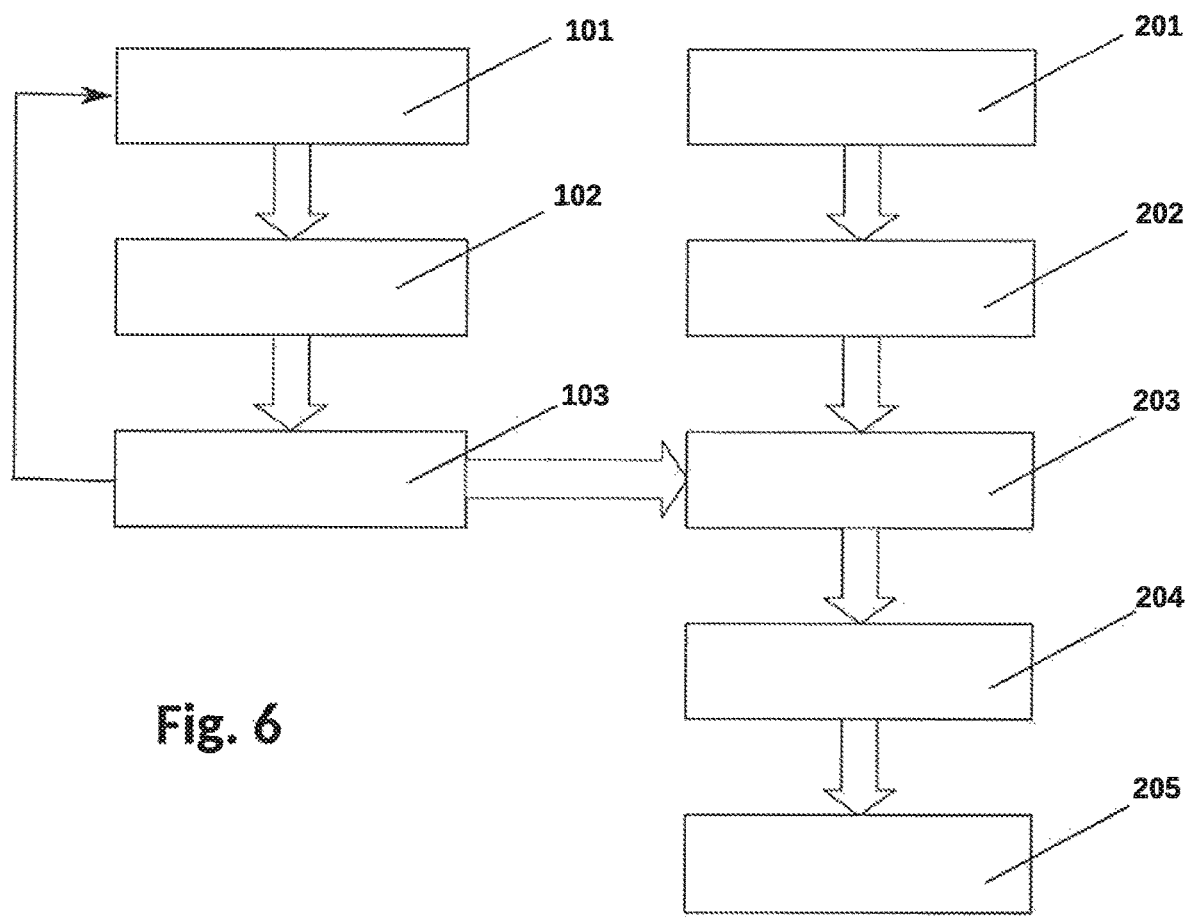
FIG. 6 shows a flowchart of the method according to the invention for producing an FPC reference body in a preferred embodiment variant.

FIG. 6 shows a preferred procedural sequence for producing an FPC reference body 26 with an artificially generated delamination 24. In a step 101, a first FPC layer 1 is placed on a mold carrier 2 in an uncured state to generate an insert. In order to form a recess 4, a molding tool 5 can be provided in the form of a projection 6 on the mold carrier 2 or in the form of a small metal plate. In a step 102, the first FPC layer 1 is precured, so as to generate the first insert 3. In a step 103, but one which is not absolutely necessary, the first insert 3 can be trimmed to a specific size. The first insert 3 is thus generated by the steps 101-103. Additional inserts, in particular the second insert 9, can be generated by again applying the steps 101-103 (as denoted by the arrow). In a step 201, the first 10 and the second 12 FPC layers are placed on a mold carrier 2 in an uncured state. In a step 202, the first 11 and the second 13 clearances are cut out of the first 10 and second 12 FPC films. In a step 203, the first 3 and second 9 inserts are inserted into the first 11 or second 13 clearance. In a step 204, at least one FPC base layer 15 can be added to the one side of the arrangement comprised of the first 10 and second 12 FPC film and/or at least one final FPC layer 16 can be added to the other side of the arrangement comprised of the first 10 and second 12 FPC film, if needed. In a step 205, the entire arrangement comprised of the first 10 and second 12 FPC film, the first 3 and second 9 inserts and any FPC base layers 15 and/or final FPC layers 16 is cured completely via a curing method suitable for the used FPC material.

Figure 7:
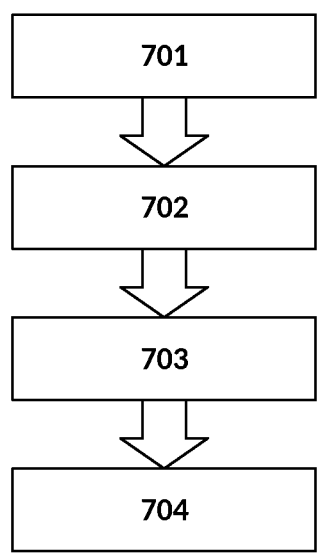
FIG. 7 shows a flowchart of an NDT test method with an FPC reference body produced with the inventive method according to claims 1 to 10.

FIG. 7 shows a preferred procedural sequence of an NDT testing procedure with an FPC reference body 26. In a step 701, an FPC reference body 26 is produced via the procedural sequence according to FIG. 6. In a step 702, the reference body is tested with a nondestructive test method, for example a thermographic method or an ultrasound method, in order to detect and measure the artificially generated delamination 24 in the FPC reference body 26. Reference values can be established in this way. In a step 703, an FPC component comprised of FPC material, in particular an aircraft component, is tested with the same nondestructive test method to obtain test results. In a step 704, the test results from step 703 are compared with the reference values from step 702, in order to in this way be able to evaluate the FPC component in relation to any component defects, in particular a delamination. For this purpose, signal amplitudes or other signal types generated by the nondestructive test method are preferably compared with each other. If a defined threshold that can be derived from the reference values is exceeded, a defective FPC component can be detected.

The invention claimed is:

1. A method for producing a fiber-plastic composite reference body for simulating a delamination for a nondestructive testing of FPC components, with the following steps:
   i. Producing a first insert for the FPC reference body by:
      a. arranging a first FPC layer;
      b. forming a recess in the first FPC layer; and
      c. precuring the first FPC layer to obtain the first insert for the FPC reference body;
   ii. Producing a second insert for the FPC reference body by:
      a. arranging a second FPC layer; and
      b. precuring the second FPC layer to obtain the second insert for the FPC reference body;
   iii. Providing at least one first FPC film with a first clearance and at least one second FPC film with a second clearance;
   iv. Inserting the first insert into the first clearance of the at least one first FPC film and inserting the second insert into the second clearance of the at least one second FPC film;
   v. Curing an arrangement comprised of the at least one first FPC film with the first insert and the at least one second FPC film with the second insert, wherein a delamination is simulated at the recess in the first FPC layer of the first insert.

2. The method according to claim 1, wherein at least one FPC base layer is provided on the one side of the arrangement comprised of the at least one first FPC film and the at least one second FPC film and/or at least one final FPC layer is provided on the other side of the arrangement comprised of the at least one first FPC film and the at least one second FPC film.

3. The method according to claim 1, wherein the first insert comprises a circumferential peripheral surface around the recess.

4. The method according to claim 3, wherein the circumferential peripheral surface is designed symmetrically around the recess, and wherein the ratio between the width of the circumferential peripheral surface and the width of an opening cross sectional surface of the recess, the opening cross sectional surface being bordered by the circumferential peripheral surface, measures essentially between 0.1 and 10.

5. The method according to claim 1, wherein the maximum height of the recess is smaller than the thickness of the at least one first FPC film.

6. The method according to claim 1, wherein the recess is formed by applying the first FPC layer on a molding tool before precuring the first FPC layer.

7. The method according to claim 6, wherein a plate part is provided as the molding tool.

8. The method according to claim 6, wherein a projection on a mold carrier is provided as the molding tool.

9. The method according to claim 6, wherein, prior to applying the first FPC layer, the molding tool is provided with a release means.

10. The method according to claim 1, wherein another recess is formed in the second FPC layer.

11. A method for the nondestructive testing of an FPC component, with the following steps:
    producing a fiber-plastic composite reference body in a method according to claim 1;
    testing the FPC component with a nondestructive test method; and
    comparing measurement results from the nondestructive test method for the FPC component with reference values for the FPC reference body.

12. The method according to claim 1, wherein the FPC components are aircraft components.

13. The method according to claim 3, wherein the circumferential peripheral surface is essentially even.

14. The method according to claim 1, wherein the maximum height of the recess is smaller than the thicknesses of all FPC films and FPC layers.

15. The method according to claim 3, wherein the circumferential peripheral surface is designed symmetrically around the recess, and wherein the ratio between the width of the circumferential peripheral surface and the width of an opening cross sectional surface of the recess, the opening cross sectional surface being bordered by the circumferential peripheral surface, measures essentially between 2 and 8.

16. The method according to claim 7, wherein the plate part is a metal plate part.

17. The method according to claim 9, wherein the release means is a liquid release agent or a separating foil.

18. The method according to claim 11, wherein the FPC component is an aircraft component.

19. The method according to claim 11, wherein the nondestructive test method is a thermographic method.

* * * * *